United States Patent [19]

Leist

[11] 4,432,365
[45] Feb. 21, 1984

[54] PHYSIOLOGICAL SENSING UNIT

[75] Inventor: Helmut Leist, Freiburg im Breisgau, Fed. Rep. of Germany

[73] Assignee: 501 Hellige GmbH, Freiburg im Breisgau, Fed. Rep. of Germany

[21] Appl. No.: 257,804

[22] Filed: Apr. 27, 1981

[30] Foreign Application Priority Data

May 16, 1980 [DE] Fed. Rep. of Germany ....... 3018863

[51] Int. Cl.$^3$ ............................................. A61B 5/00
[52] U.S. Cl. ................................... 128/635; 204/403; 204/408
[58] Field of Search ............................... 128/635, 401; 204/195 B, 195 P, 195 R, 407, 408, 415, 434; 219/510

[56] References Cited

U.S. PATENT DOCUMENTS

| | | | |
|---|---|---|---|
| 3,838,248 | 9/1974 | Uchida et al. | 219/510 X |
| 4,142,529 | 3/1979 | Latenser et al. | 128/401 |
| 4,195,415 | 4/1980 | Livings et al. | 219/510 X |
| 4,280,505 | 7/1981 | Dali et al. | 128/635 |
| 4,290,431 | 9/1981 | Herbert et al. | 128/635 |
| 4,334,541 | 6/1982 | Leist et al. | 128/635 |

FOREIGN PATENT DOCUMENTS 9129 4/1980 European Pat. Off. ........... 128/635

Primary Examiner—Lee S. Cohen
Attorney, Agent, or Firm—Robert A. Seldon

[57] ABSTRACT

Disclosed herein is a physiological, electrically heated, thermostatically controlled sensing unit of the type used in the medical field for measuring blood contents, such as oxygen. A typical unit comprises a housing for application to the skin of a living being, an electric heater element within the housing, and a temperature-responsive switching circuit, also accommodated within the housing. The switching circuit automatically disconnects a power supply to the heater element when the skin temperature exceeds an adjustable predetermined threshold level. The power supply for the switching circuit is directly connected to the power supply for the heater element within the housing.

12 Claims, 4 Drawing Figures

PHYSIOLOGICAL SENSING UNIT

TECHNICAL FIELD OF THE INVENTION

This invention is concerned with a hyperemia-inducing physiological sensing unit of the type having a heater element and a thermostatically controlled switch for preventing overheating.

DESCRIPTION OF THE PRIOR ART

For medical diagnostic purposes, various types of physiological sensing units may be employed. Units of this type to which that of the present invention pertains are used for transcutaneous measurement and monitoring of various physiological phenomena, i.e. without puncturing the skin of the patient. Typical applications are measurements of blood flow, blood oxygen content, sugar content, alcohol content, carbon dioxide content, blood pH, etc. During use, such devices are secured temporarily to the skin of the patient. The sensing unit is heated by an internal heater element for the purpose of local hyperemization at the location where the sensing unit is in contact with the skin of a patient.

Usually, the internal heater element is electrically energized, although diathermically-heated elements are known. Ordinarily, the desired temperature range is in the order of 37 to 45 degrees C. (98.6 degrees to 113 degrees F.) and is controlled by a suitable thermostat. As it is desirable that the sensing unit itself be constrained to minimal dimension, it is conventional that only the sensor element proper, typically a Clark element, the heater element and a heat sensor, such as a small thermistor, are mounted in the physiological sensing unit. The heater controls, such as a thermostat, temperature indicator and heater power supply are mounted in a separate, remote control module. The control module is connected to the physiological sensing unit by a multiconductor cable which should also be of small dimensions, particularly with respect to its cross section and the number of connecting conductors.

With any electrical control device, there is always the danger of a control circuit malfunction. Thus, if the thermostat itself were to malfunction, or if the temperature sensing lines from the thermistor failed, the patient would be endangered if the physiological sensing unit were overheated.

It is known to add a second, backup temperature sensor and thermostat to take over in the event that the primary temperature control circuit fails. However, such an arrangement requires additional conductors, as well as additional complexity in the remote control module.

Accordingly, more recent designs provide a safety switch that is built into the sensing unit itself, for automatically cutting off the power supply to the heater element in the sensing unit, independently of the heater supply control system, in the event of a catastrophic failure of the conventional thermostatic temperature control circuitry.

One such physiological sensing unit having a heating arrangement of electrical nature, in which a switch has been provided for preventing overheating for reasons of safety is disclosed in patent application Ser. No. 130,639 filed Mar. 17, 1980. The switch disables the heater, for example by interrupting energizing current flow or short-circuiting the supply lines to the heater element, whenever a predetermined threshold level of temperature is exceeded. It is thus known to build temperature sensors into transcutaneous physiological sensing units for medical diagnostic purposes. These temperature sensors, associated with temperature control switches directly built into the sensing unit, guarantee a well-determined operational range of temperatures, for example of about 37 to 45 degrees C. (i.e. 98.6 degrees to 113 degrees F.).

When an electronic switch which is directly built into the sensing unit is used in accordance with the above-mentioned, recently developed designs, then an operating voltage is needed for the electronic switch. If this operating voltage is derived from the power supply section of the measuring instrument accommodated in the remote control module, then at least one additional conductor is needed which connects the remote control module and the sensing unit. This means that the cable which interconnects the control module with the sensing unit must include at least one additional conductor. It is possible to select a circuit layout for the electronic switch such that the heater power supply is interrupted whenever such additional connecting conductor becomes defective. However, the total investment in the instrument is increased and this arrangement constitutes a regress from the point of view of an important, continuously pursued goal, namely that of maintaining the number of connecting conductors in the cable at a minimum.

SUMMARY OF THE INVENTION

Starting out from the state of the art set forth above, the invention is concerned with the problem of providing an electronic switch which is built into a physiological sensing unit, which switch cooperates with a temperature control circuit, without reducing the safety of operation by additional structural investments and also without a separate current supply line in the cable which interconnects the remote control module, or unit, with the sensing unit.

In accordance with a broad aspect of the invention, a physiological, electrically heated, thermostatically controlled sensing unit comprises a housing for application to the skin of a living being, an electric heater element and a temperature-responsive switching circuit for the heater element both accommodated within the housing, and common supply means, such as terminals and connecting lines including only one pair of inputs, for applying electrical energizing power from an external, common source to both the heater element and the switching circuit.

In accordance with a somewhat more detailed summarization, a physiological, electrically heated, thermostatically controlled sensing unit of the invention for application to the skin of a living being comprises, accommodated within a housing, an electric heater element, electronic switching means, suitably a transistor whose collector-emitter path is connected in series with the heater element, for automatically disconnecting power supply to the heater element when the skin temperatures exceeds an adjustable predetermined threshold level, a temperature-responsive switching circuit for operating the switching means, i.e. the transistor, input means for connecting an external source of power to the temperature-responsive switching circuit, and means for deriving energization power for the electric heater element from the input means.

The solution in accordance with the invention, namely the concept of supplying power for the electronic switch from the heater current supply to the sensing unit and the concept of accommodating the temperature control circuit, referred to herein as the temperature-responsive switching circuit, for the electronic switch within the sensing unit, results in the avoidance of at least one additional connecting conductor or line in the connecting cable, but also results in the avoidance of the disadvantageous increase in the thickness of the connecting cable between the remote control module, or unit, and the sensing unit, thereby to also solve the safety problem which would inherently be present due to an additional supply line. Overheating the measuring unit becomes impossible by virtue of the provision of direct supply of power to both the temperature-sensitive switching circuit, as well as the heater element, with the electronic switch controlling it, from the supply lines for connection to an external power source. In this manner, interruption of current supply to the temperature-controlled electronic switch must of necessity be simultaneously accompanied by disconnection of current supply to the heater.

Thus, the invention offers the advantage of avoiding an additional supply line which would diminish the safety aspect and the invention also achieves the result that, in case of supply line defect, both the temperature-controlled switch and the heater element are deenergized simultaneously, so that, in the case that only the temperature-controlled switch does not properly operate, the danger of overheating is avoided.

In accordance with an advantageous embodiment of the invention, a simple additional circuit feature of the temperature control arrangement leads to the result that current supply to the heater is interrupted either completely until steps are taken by a user, i.e. operator of the instrument, or interruption continues at least until the temperature has descreased to reach a level below a threshold temperature, which is adjusted by adjusting one of the temperature control circuit components.

The electronic temperature-controlled switch with the associated temperature-responsive switching circuit in accordance with the invention can be accommodated in a very small space within the housing of the physiological sensing unit, as it may be an integrated circuit or a hybrid circuit.

To summarize, it can be seen that the present invention is based upon the recognition that a physiological sensing unit of the type contemplated, with a minimum of supply lines within the cable of supply lines and simultaneously increased safety for the patient, involves a design wherein the heater and the temperature-responsive switching circuit for the heater element operate—under normal conditions—under control of an external thermostatic control system, while—in case of overheating—the system operates as its own safety device to deenergize the heater element in case of overheating which, with known arrangements, result from failure of power supply lines to the heater element or failure of the thermostatic control system.

BRIEF DESCRIPTION OF THE DRAWINGS

The invention and advantageous details of a preferred embodiment illustrated by way of example are described below in more detail, with reference to the drawing. In the drawing.

Mutually corresponding elements in the figures are identified by the same reference characters.

DETAILED DESCRIPTION OF A PREFERRED EMBODIMENT

Figure 1:
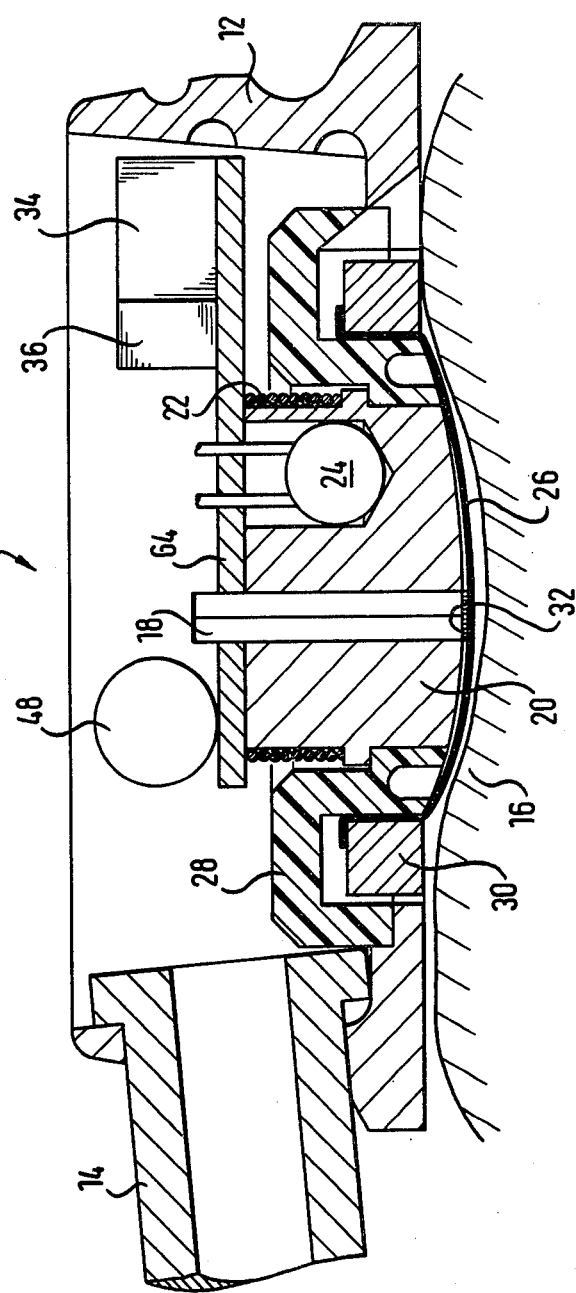
FIG. 1 is a schematic, axial cross-sectional view of a sensing unit in accordance with the invention.

Referring now to FIG. 1, there is shown a physiological sensing unit 10, whose component parts are accommodated within a housing 12 and which is normally coupled to a conventional, remote control unit (not shown) by means of a multiconductor cable 14 for applying electrical power to, and for receiving measurement signals from, the sensing unit 10. Physiological sensing unit 10 may be a polarometer for the transcutaneous determination of the concentration of gases, such as oxygen, in the blood of a patient. Typical sensors are of the Clark type and are usually in the form of a circular plate a few centimeters in diameter. During use, the housing 12 accommodating the essential components of the sensing unit is placed in direct contact with the skin 16 of a patient.

In the housing 12 of sensing unit 10 of FIG. 1, a conventional triple electrode 18, preferably of platinum, is mounted inside, but isolated from a silver block 20. A heater element, shown as coil 22, surrounds silver block 20. These, like all other components of the sensing unit, are maintained in position within the housing 12 by means of brackets or other mechanical structures of known nature, omitted for the purpose of clarity of the drawing. Conductors (not shown) in cable 14 transmit the polarometric current to a suitable recording or indicating instrument mounted in the remote control module (not shown). Other conductors (also not shown) in cable 14 provide power from an external source to the heater element 22 via an electronic switch 36 by a controlled temperature-responsive circuit 34 described below in connection with FIG. 2. In FIG. 1, it will be noted, the various circuit components are illustrated schematically only, as the remaining figures show the circuit in detail. A temperature-sensing element, suitably a temperature-responsive resistor 24 such as a thermistor, is mounted in the sensing unit 10 to cooperate with the remaining components of the temperature-responsive switching circuit 34 and electronic switch 36 to perform the function as an emergency cut-off arrangement in case of skin overheating. An additional temperature-responsive element (not shown), e.g. a temperature-responsive resistor of the same type as resistor 24 is arranged within the silver block 20 and connected via a separate conductor pair of multiconductor cable 14 to a thermostat to maintain the skin temperature within a predetermined range.

A thin membrane 26 covers the lower surfaces of the silver block 20 and the triple electrode 18. Membrane 26 is held in place and is sealed against the silver block 20 by a retaining ring 28 which, in turn, is secured by a pressure ring 30 to silver block 20. A suitable electrolyte is contained in the space 32 between the membrane 26 and triple electrode 18. The membrane 26 may be of plastic, such as polyethylene, polypropylene or polytetrafluoroethylene. The essential properties of membrane 26 are that it be permeable to the diffused gases to be measured, but impermeable to the electrolyte.

Normally, the temperature of physiological sensing unit 10 is maintained constant by means of the external thermostat in known manner. The temperature-responsive switching circuit 34 of the present invention accommodated within the housing 12, under control of temperature-sensitive resistor 24 connected into the circuit as described below in connection with the remaining FIGS. 2, 3 and 4, in the event of malfunction, disconnects or short-circuits the heater supply circuit until the malfunction has been corrected as is also explained further below.

Figure 2:
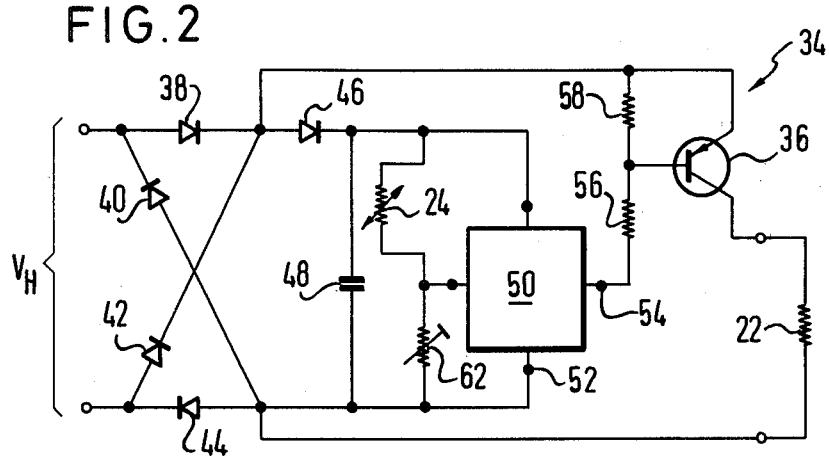
FIG. 2 is a schematic diagram of a temperature-responsive switching circuit accommodated within the housing of the unit of FIG. 1 and controlling an electronic switch.

The circuit diagram of FIG. 2 illustrates, in detail, the electronic switch, shown as switching transistor 36, whose collector-emitter path is connected in series with the heater element 22, as well as the temperature-responsive switching unit 34. The series network of transistor 36 and heater element 22 is connected between the DC output terminals of a full-wave bridge rectifier formed by diodes 38, 40, 42 and 44. This full-wave rectifier is employed for rectifying the input voltage $V_H$ for the heater element 22 derived from an external power source and applied to the input terminals of the circuit, as shown. Whenever the voltage $V_H$ is unidirectional, the bridge rectifier of diodes 38, 40, 42 and 44 may be omitted.

In the circuit in accordance with FIG. 2, a series network, comprising a diode 46 and a capacitor 48, shown separately in FIG. 1, and connected between the DC output terminals of the full-wave rectifier, serves for smoothing the operating voltages for the threshold switch, for example a Schmitt trigger 50, whose output circuit is connected between terminals 52 and 54, in series with resistors 56 and 58. As can be seen, the operating point of the base of transistor 36 is determined by the instantaneous ratio of resistances 58: [56+(52→54)], wherein (52→54) designates the resistance between the terminals 52 and 54 of the threshold switch 50.

Figure 3:
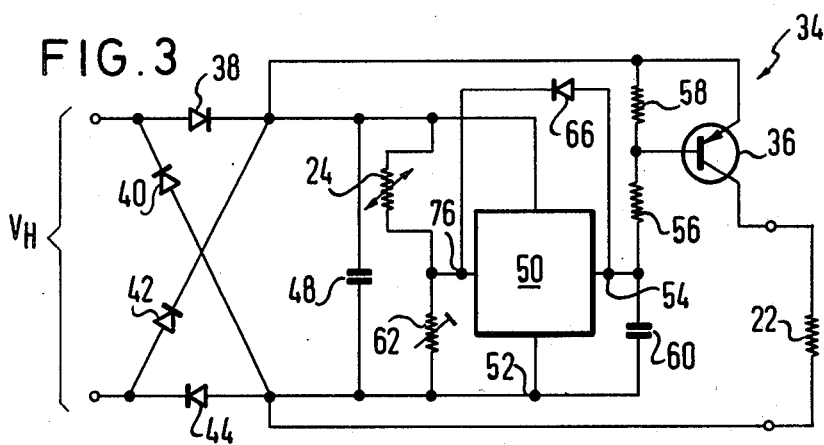
FIG. 3 illustrates a slightly modified embodiment of the circuit of FIG. 2, with an additional feature for achieving and maintaining disconnection of the energization power supply to the heater in the sensing unit subsequent to a temperature increase beyond the predetermined threshold value and prevailing until an operator restores proper working conditions.
Figure 4:
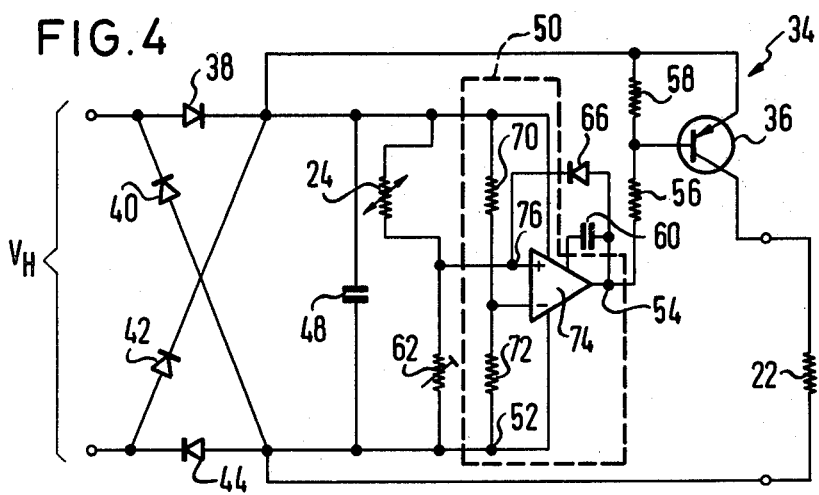
FIG. 4 corresponds to the circuit diagram of FIG. 3, modified to show details of an example of the threshold switch of the circuit of FIGS. 2 and 3.

The capacitor 60 which, in FIGS. 3 and 4, is shown connected across the output terminals of the threshold switch 50 is used for suppressing disturbances, i.e. noise, and for delaying response to the switching off or short-circuiting of the supply voltage $V_H$ for the heater element 22.

The switching point of the threshold switch 50 is determined by the ratio of the resistance values of the two resistors 24 and 62 which are connected in series between the input terminals via which power, illustrated as the voltage $V_H$, is supplied to the circuit. The resistor 24 is temperature-responsive and, thus, by way of example, a thermistor and disposed as close as possible to the measuring surface of the sensing unit, as shown in FIG. 1, and similar as the other temperature-responsive element controlling the thermostat. The adjusting resistor 62 can be set to establish the switching threshold temperature for the threshold switch 50.

It will be understood that the entire circuit of FIG. 2, with the exception of the heater element 22, the capacitor 48, because of its size, and the temperature-responsive resistor 24 can suitably constitute an integrated circuit upon a printed circuit board 64, as schematically indicated in FIG. 1 which shows a block diagram representing the temperature-responsive switching circuit 34 of FIG. 2.

In the embodiment in accordance with FIG. 3, a diode 66 is connected between the output 54 and the control input 76 of the threshold switch 50, which causes continuing disconnection upon transgression of an adjustable switching threshold which is maintained until the cause of possible overheating of the sensing unit 10 has been removed by an operator. The diode 66 achieves a thyristor effect by virtue of a strong positive feedback.

FIG. 4 illustrates details of a practical embodiment for the threshold switch 50. As shown, the series network of resistors 24 and 62 can be complemented to become a resistor bridge circuit by the parallel-connected addition of series resistors 70 and 72 whose central junctions are connected to the two inputs of a differential amplifier 74. A comparator can be used instead of the differential amplifier.

The circuit in accordance with FIG. 4 operates in the following manner:

When the temperature of resistor 24, and therewith its resistance value, decreases, the voltage at junction 76 rises above the predetermined threshold value which is determined by the ratio of resistance values of resistors 70 and 72, the output at terminal 54 of differential amplifier 74 becomes positive and therewith transistor 36 becomes nonconductive and thus interrupts current through the heater element 22. Simultaneously, the non-inverting input 76 of differential amplifier 74 is brought into a more positive potential by positive feedback through diode 66, which effect causes proper switching conditions and prevents a lowering of the potential at junction 76 as a result of the clamping action of diode 66, even when the temperature of resistor 24 again decreases and its resistance value again increases. In this circuit, the capacitor 60 operates as an integrating component in association with the output stage of the differential amplifier 74.

It will, thus, be seen that normally, i.e. in the absence of catastrophic failure, the circuit operates as to maintain the electronic switch transistor 36 in closed condition, i.e. conducting condition, and in case of failure or malfunction of the thermostatic control the circuit interrupts power supply to the heater element 22 from a time when the threshold level of skin temperature has been reached until a time when the temperature decreases to a level below the threshold temperature level. In practice, the duration until a temperature will be reached again which is lower than the threshold level will be a function of the amount of switching hysteresis, as introduced by the Schmitt trigger, i.e. threshold switch 50. Moreover, interruption of heater current supply is sustained until an operator remedies malfunction by the fact that the output from the threshold switch 50 is connected to the non-inverting input of the threshold switch 50 over the diode 66 in order to maintain the condition of disconnection as long as the skin temperature exceeds the threshold level. Thus, the diode branch constitutes a network associated with the switching circuit for maintaining current supply to the heater element interrupted from the time a threshold level of skin temperature has been reached until an operator has restored normal operating conditions.

Though the invention is described herein in connection with a specific circuit implementing its basic concept, various modifications can be made within the scope of the principles disclosed.

What is claimed is:

1. A physiological, electrically heated thermostatically controlled sensing unit, comprising:
a housing;
a sensing element supported within the housing for application to the skin of a living being;
an electric heater element located within the housing;
first temperature-responsive switch means located in the housing and adapted for coupling to a control circuit remote from the sensing unit for maintaining the sensing unit at a preselected temperature level in conjunction with said heater element;
a second switch for interrupting energization of the electric heater element;
temperature-responsive control circuit means contained in the housing for operating the second switch to interrupt energization of the electric heater element if the temperature of the sensing unit exceeds the pre-selected temperature level to reach a predetermined threshold value;
power supply means for the control circuit means;
power supply means for the electric heater element; and
means for coupling the sensing element to monitoring equipment.

2. Sensing unit in accordance with claim 1 wherein the second temperature-responsive switch means comprises a transistor whose collector-emitter path is connected in series with the heater element.

3. Sensing unit in accordance with claim 3, wherein the control circuit means interrupts the power supply means to the heater element from a time when the threshold level of skin temperature has been reached until a time when the temperature decreases to a level below the threshold temperature level.

4. Sensing unit in accordance with claim 1, wherein the control circuit means deenergizes the heater element from a time when the threshold level of skin temperature is reached and for a duration until a temperature will be reached again which is lower than the threshold level by the amount of switching hysteresis.

5. Sensing unit in accordance with claim 1, comprising, a threshold switch forming part of the control circuit means and controlling the second switch.

6. Sensing unit in accordance with claim 5, comprising a resistor bridge network and wherein the input to the threshold switch is connected to the output branch of the resistor bridge network whose input is the heater element power supply means one of the branches of the bridge network containing a temperature-responsive resistor.

7. Sensing unit in accordance with claim 5 or claim 8, wherein the threshold switch is a differential amplifier.

8. Sensing unit in accordance with claim 7, wherein the output from the differential amplifier is connected to the non-inverting input of the differential amplifier via a diode, in order to maintain the condition of disconnection as long as the skin temperature exceeds the threshold level or until the power supply is disconnected.

9. Sensing unit in accordance with claim 1 comprising network means associated with the control circuit means for maintaining current supply to the heater element interrupted from the time a threshold level of skin temperature has been reached until an operator has restored normal operating conditions.

10. Sensing unit in accordance with claim 1 comprising capacitor means for delaying response of the control circuit means.

11. Sensing unit in accordance with claim 1, comprising a noise suppressor means for preventing response of the second switch to noise signals.

12. Sensing unit in accordance with claim 1, comprising network means for permitting supplying the control circuit means and the heater element from a source of pulsating DC power.

* * * * *